(12) United States Patent
Tanaka et al.

(10) Patent No.: US 7,638,340 B2
(45) Date of Patent: Dec. 29, 2009

(54) METHOD OF ELIMINATING REACTIVITY OF LIPOARABINOMANNAN AND APPLICATION OF THE SAME

(75) Inventors: Shigenori Tanaka, Tokyo (JP); Shoji Takahashi, Tokyo (JP)

(73) Assignee: Seikagu Corporation, Chiyoda-ku, Tokyo (JP)

( * ) Notice: Subject to any disclaimer, the term of this patent is extended or adjusted under 35 U.S.C. 154(b) by 0 days.

(21) Appl. No.: 11/993,214

(22) PCT Filed: Jun. 21, 2006

(86) PCT No.: PCT/JP2006/312420

§ 371 (c)(1),
(2), (4) Date: Dec. 19, 2007

(87) PCT Pub. No.: WO2006/137444

PCT Pub. Date: Dec. 28, 2006

(65) Prior Publication Data

US 2009/0117661 A1    May 7, 2009

(30) Foreign Application Priority Data

Jun. 22, 2005    (JP) .............................. 2005-182667

(51) Int. Cl.
*G01N 33/92* (2006.01)
(52) U.S. Cl. .............................. 436/71; 436/73; 436/79; 436/175; 435/18; 536/18.2
(58) Field of Classification Search .................. 436/71, 436/73, 79, 174, 175; 422/61; 435/18, 34; 536/18.2
See application file for complete search history.

(56) References Cited

U.S. PATENT DOCUMENTS

| 5,378,610 A | | 1/1995 | Tanaka et al. |
| 5,389,547 A | * | 2/1995 | Tanaka et al. .................. 436/94 |
| 5,648,230 A | | 7/1997 | Tamura et al. |
| 2005/0069972 A1 | * | 3/2005 | Castro et al. ................... 435/34 |
| 2007/0154979 A1 | * | 7/2007 | Tanaka et al. .................. 435/34 |
| 2009/0011448 A1 | * | 1/2009 | Oda et al. ....................... 435/13 |

FOREIGN PATENT DOCUMENTS

| JP | 04-136763 | 5/1992 |
| JP | 07-239332 | 9/1995 |
| JP | 08-075751 | 3/1996 |
| WO | WO 03/048383 | 6/2003 |

OTHER PUBLICATIONS

Gilleron, et al. "Characterization of a Truncated Lipoarabinomannan from the Actinomycete *Turicella otitidis*," *Journal of Bacteriology*, vol. 187, No. 3, pp. 854-861, Feb. 2005.
International Search Report dated Jul. 5, 2006.

* cited by examiner

*Primary Examiner*—Maureen M Wallenhorst
(74) *Attorney, Agent, or Firm*—Knobbe, Martens, Olson & Bear, LLP

(57) ABSTRACT

A method of eliminating the reactivity of lipoarabinomannan contained in a sample to a *Limulus* reagent including at least the step of allowing the sample containing lipoarabinomannan to coexist together with a metal salt or a buffer; and a method of assaying an endotoxin and a method of detecting an endotoxin-associated disease by using the above-described method.

12 Claims, 6 Drawing Sheets

METHOD OF ELIMINATING REACTIVITY OF LIPOARABINOMANNAN AND APPLICATION OF THE SAME

CROSS-REFERENCE TO RELATED APPLICATIONS

This application is the U.S. National Phase under 35 U.S.C. § 371 of International Application PCT/JP2006/312420, filed Jun. 21, 2006, which was published in a non-English language, which claims priority to JP 2005-182667, filed Jun. 22, 2005.

TECHNICAL FIELD

The present invention relates to a method of eliminating the reactivity of lipoarabinomannan to a *Limulus* reagent, a method of assaying endotoxin in a sample containing lipoarabinomannan, a method of detecting an endotoxin-associated disease by making use of the above method, a kit for assaying endotoxin and a kit for diagnosing an endotoxin-associated disease, which can be used in these methods, and the like.

BACKGROUND ART

The following abbreviations are used herein:
LAM: lipoarabinomannan
Et: endotoxin
BG: (1→3)-β-D-glucan.

A *Limulus* reagent (also called a lysate reagent) is a reagent containing a horseshoe crab amoebocyte lysate as a main component, and is used for the detection and measurement of Et and BG. Since the *Limulus* reagent has reactivity with Et and BG, when the *Limulus* reagent and the substances contact with one another, a cascade reaction in which various factors in the *Limulus* reagent are concerned (hereinafter, referred to as "*Limulus* reaction") is induced, so these substances can be detected and measured by detecting this reaction.

On the other hand, it is known that LAM is a cell wall component specific to acid-fast bacteria (e.g., *tubercle bacillus*).

Patent Document 1 discloses an Et stabilizer containing an alkaline earth metal salt as an active ingredient and a method of assaying Et using the Et stabilizer. However, this document neither discloses nor teaches that the alkaline earth metal salt has an eliminating effect on the reactivity of LAM to a *Limulus* reagent.

Patent Document 2 discloses a method of assaying Et, which is characterized by treating plasma or blood serum with an aqueous solution of a mixture of calcium chloride and potassium hydroxide to prepare a specimen solution. However, the document neither discloses nor teaches that calcium chloride has an eliminating effect on the reactivity of LAM to a *Limulus* reagent.

In addition, a freeze-dried product of a *Limulus* reagent is typically dissolved in water, a specimen solution, a buffer, or the like and then used. However, there is no finding that the buffer has an eliminating effect on the reactivity of LAM to the *Limulus* reagent.

Further, Patent Document 3 describes a method of assaying a substance reactive to a *Limulus* reagent in a specimen using a *Limulus* reagent containing, as an active ingredient, a compound having a specific structure to show a buffer action and a horseshoe crab amoebocyte lysate. However, the document neither discloses nor teaches that the above compound has an eliminating effect on the reactivity of LAM to the *Limulus* reagent.

Patent Document 1: JP-A-8-75751
Patent Document 2: JP-A-4-136763
Patent document 3: JP-A-7-239332

DISCLOSURE OF THE INVENTION

The inventors of the present invention have found that LAM reacts with a *Limulus* reagent and thus a quantitative assay of Et without any influence of LAM is difficult when a sample containing both Et and LAM is used. The present invention intends to provide a method of eliminating the reactivity of LAM to a *Limulus* reagent, a method of assaying Et in a sample containing LAM, a method of detecting Et-associated disease by making use of the above method, a kit for assaying Et and a kit for diagnosing an Et-associated disease, which can be used in these methods, and the like.

As a result of intensive studies toward solving the above-mentioned problems, the inventors of the present invention have found that the coexistence of a sample containing LAM with a metal salt or a buffer leads to the elimination of the reactivity of LAM in the sample to a *Limulus* reagent. Consequently, the inventors of the present invention have attained to provide the method of eliminating the reactivity of LAM to a *Limulus* reagent, the method of assaying Et in a sample containing LAM, the method of detecting Et-associated disease by making use of the above method, the kit for assaying Et and a kit for diagnosing Et-associated disease, which can be used in these methods, and the like.

Specifically, the present invention provides any one of the methods and kits as described in the following items (1) to (17).

(1) A method of eliminating reactivity of LAM in a sample containing LAM to a *Limulus* reagent, comprising at least a step of allowing the sample to coexist with a metal salt (hereinafter, referred to as Elimination method 1 of the present invention).

(2) The method according to (1), wherein said metal salt is one or more metal salts selected from sulfate salts, metal chlorides, and nitrate salts.

(3) The method according to (2), wherein said metal salt is one or more metal salts selected from the group consisting of sodium sulfate, magnesium sulfate, potassium sulfate, sodium chloride, magnesium chloride, potassium chloride, calcium chloride, sodium nitrate, and potassium nitrate.

(4) The method according to any one of (1) to (3), wherein said metal salt is coexistent at a final concentration of 30 mM or more in the sample.

(5) A method of eliminating reactivity of LAM in a sample containing LAM to a *Limulus* reagent, comprising at least a step of allowing the sample to coexist with a buffer (hereinafter, referred to as Elimination method 2 of the present invention).

(6) The method according to (5), wherein said buffer is one or more buffers selected from the group consisting of tris(hydroxymethyl)aminomethane, 2-[4-(2-hydroxyethyl)-1-piperazinyl]ethanesulfonic acid, N-tris(hydroxymethyl)methyl-2-aminoethanesulfonic acid, 2-hydroxy-3-[4-(2-hydroxyethyl)-1-piperazinyl]propanesulfonic acid monohydrate, N-[tris(hydroxymethyl)methyl]glycine, N,N-bis(2-hydroxyethyl)glycine, and imidazole.

(7) The method according to (5) or (6), wherein said buffer is coexistent at a final concentration of 100 to 300 mM in the sample.

(8) A method of assaying Et in a sample containing LAM and Et using a *Limulus* reagent, comprising at least a step of eliminating reactivity of LAM to the *Limulus* reagent by the method according to any one of (1) to (7) (hereinafter, referred to as Et-assay method of the present invention).

(9) A method of assaying Et, comprising at least the following steps (a) and (b):
  (a) allowing a sample containing Et and LAM to coexist with a metal salt or a buffer; and
  (b) contacting the sample with a *Limulus* reagent after the coexistence to detect a *Limulus* reaction initiated by Et.

(10) A method of assaying Et, comprising at least the following steps (a) and (b):
  (a) allowing a *Limulus* reagent to coexist with a metal salt or a buffer; and
  (b) contacting a sample containing Et and LAM with the *Limulus* reagent after the coexistence to detect a *Limulus* reaction initiated by Et.

(11) The method according to any one of (8) to (10), wherein said *Limulus* reagent is an Et-specific *Limulus* reagent.

(12) A method of detecting an Et-associated disease, comprising using the method according to any one of (8) to (11) (hereinafter, referred to as Disease detection method of the present invention).

(13) A kit for assaying Et, which is used for an assay of Et with a decreased influence of LAM, comprising, as components:
  a *Limulus* reagent; and
  a metal salt or a buffer (hereinafter, referred to as Kit for assaying Et of the present invention).

(14) The kit according to (13), wherein said metal salt is one or more metal salts selected from sulfate salts, metal chlorides, and nitrate salts.

(15) The kit according to (14), wherein said metal salt is one or more metal salts selected from the group consisting of sodium sulfate, magnesium sulfate, potassium sulfate, sodium chloride, magnesium chloride, potassium chloride, calcium chloride, sodium nitrate, and potassium nitrate.

(16) The kit according to (13), wherein said buffer is one or more buffers selected from the group consisting of tris(hydroxymethyl)aminomethane, 2-[4-(2-hydroxyethyl)-1-piperazinyl]ethanesulfonic acid, N-tris(hydroxymethyl)methyl-2-aminoethanesulfonic acid, 2-hydroxy-3-[4-(2-hydroxyethyl)-1-piperazinyl]propanesulfonic acid monohydrate, N-[tris(hydroxymethyl)methyl]glycine, N,N-bis(2-hydroxyethyl)glycine, and imidazole.

(17) The kit according to any one of (13) to (16), wherein said *Limulus* reagent is an Et-specific *Limulus* reagent.

(18) A kit for diagnosing an Et-associated disease, comprising the kit according to any one of (13) to (17) (hereinafter, referred to as Kit for diagnosing disease of the present invention).

(19) A reactivity-eliminating agent to be used for eliminating reactivity of LAM to a *Limulus* reagent, comprising a metal salt as an active ingredient (hereinafter, referred to as Reactivity-eliminating agent 1 of the present invention).

(20) A reactivity-eliminating agent to be used for eliminating reactivity of LAM to a *Limulus* reagent, comprising a buffer salt as an active ingredient (hereinafter, referred to as Reactivity-eliminating agent 2 of the present invention).

DESCRIPTION OF THE PREFERRED EMBODIMENTS

Figure 1:
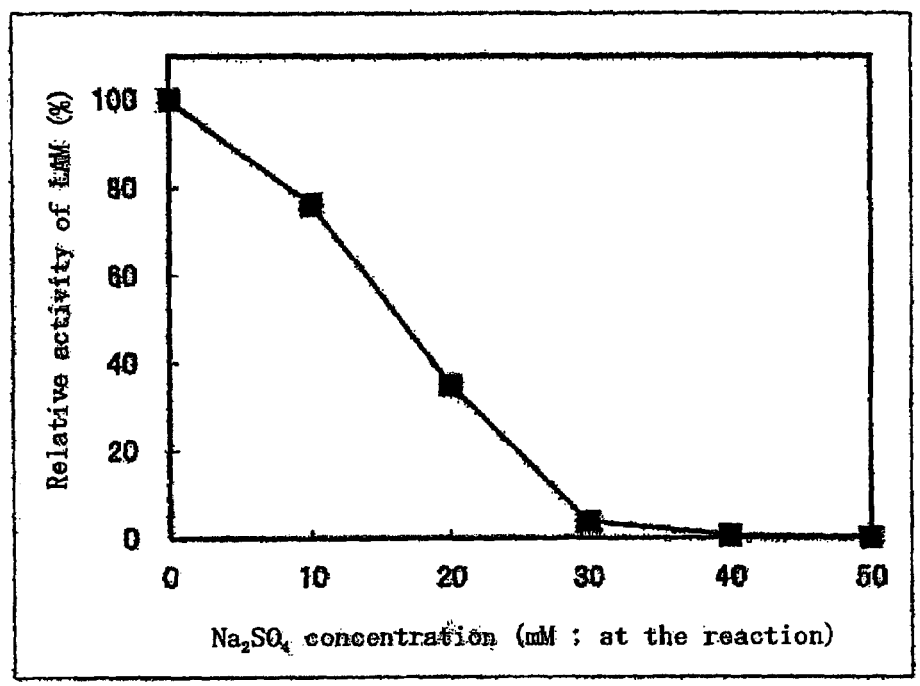
FIG. 1 is a diagram showing a relationship between the concentration of sodium sulfate and the relative activity of LAM in a *Limulus* reaction with a lysate originating from *Tachypleus tridentatus*.

<1> Elimination Method 1 of the Present Invention

Elimination method 1 of the present invention is a method of eliminating the reactivity of LAM in an LAM-containing sample to a *Limulus* reagent, comprising at least the step of allowing the sample to coexist with a metal salt.

In the description, the "LAM-containing sample" is not particularly limited so long as it is a sample that contains LAM or may contain LAM. Since LAM is a cell wall component specific to acid-fast bacteria, living cells, dead cells or cell walls of the acid-fast bacterium (e.g., tubercle bacillus), a sample which contains the cell wall component or may contain the same can be exemplified as LAM-containing sample. Examples of such a sample include *tubercle bacillus* vaccine. In addition, a "sample derived from the living body" can also be used as the "LAM-containing sample". The "sample derived from the living body" is not particularly limited either, but is preferably a body fluid. The body fluid is not particularly limited so long as it is a body fluid that contains LAM or may contain the same. Examples of the body fluid include blood (in the description, this is used as a general idea including serum and plasma), expectoration, spinal fluid, urine, sweat, saliva, tears, and synovial fluid. Of those, blood is preferable.

In this connection, when blood is used as the "sample derived from the living body", it is preferable to remove or inactivate *Limulus* reaction inhibitors in blood (serine protease, serine protease inhibitor, etc.) in advance by a conventionally known method (e.g., the method described in JP-A-58-85162).

Further, in Elimination method 1 of the present invention, the metal salt has only to be one having a function of eliminating the reactivity of LAM in an LAM-containing sample to a *Limulus* reagent. The types, number, combination, and so on of metal salts to be used are not particularly limited. The metal salt may be of a single type or may be a combination of two or more types. For example, a mixture of two or more types of metal salts may be used. In addition, the metal salt is not limited by, for example, the state or form in which the metal salt exists. For example, the metal salt may be just one in a solid state to be powderized or one being present in a state of being dissolved in a solution such as purified water. Further, the metal salt may be present in mixture with any one of the components other than the metal salt including a surfactant, an antituberculous antibody, an anti-LAM antibody, BG, carboxymethylated BG, a strong alkaline substance, Polymyxin B, colistin, concanavalin A, histidine, histamine, and a *Limulus* reagent. Here, for example, when the metal salt is present in mixture with any one of the substances such as a surfactant, an antituberculous antibody, an anti-LAM antibody, BG, carboxymethylated BG, a strong alkaline substance, Polymyxin B, colistin, concanavalin A, histidine, and histamine, a more preferable eliminating effect on the reactivity of LAM to a *Limulus* reagent can be expected. Further, for example, when the metal salt is present in mixture with a *Limulus* reagent and LAM-containing sample is a sample which contains Et or may contain Et, a *Limulus* reaction can be detected or assayed. In this case, the *Limulus* reaction is initiated by Et in the LAM-containing sample after allowing the sample to coexist with a mixture of the *Limulus* reagent and the metal salt. As a result, Et in the above sample can be assayed without the influence of LAM or with a reduced influence of LAM. For more specific description about the assay method, "<3> Et-assay method of the present invention" described later can be referred.

Specific examples of the metal salt preferably include sulfates, metal chlorides, and nitrates. Of those, one or two or more metal salts selected from the following group are more preferable.

Sodium sulfate, magnesium sulfate, potassium sulfate, sodium chloride, magnesium chloride, potassium chloride, calcium chloride, sodium nitrate, and potassium nitrate.

Of those, a metal salt including at least sodium sulfate or sodium chloride is more preferable. In this case, the metal salt may include either sodium sulfate or sodium chloride, or both of them. Particularly preferably, the metal salt includes at least sodium sulfate.

Further, in Elimination method 1 of the present invention, the concentration (concentration after the coexistence) of the metal salt in the LAM-containing sample in the step of allowing the sample to coexist with the metal salt (hereinafter, simply described as the "final concentration of the metal salt in the sample") is not particularly limited as long as the concentration can exert an action of eliminating the reactivity of LAM in the LAM-containing sample to a *Limulus* reagent. A person skilled in the art can appropriately define the final concentration depending on, for example, the type of the metal salt to be used and the degree of the above eliminating effect on the reactivity to be desired by a person who carries out Elimination method 1 of the present invention.

The higher the final concentration of the metal salt in the sample, the more the eliminating effect on the reactivity of LAM to the *Limulus* reagent. Specifically, it is preferable to allow the sample to coexist with the metal salt to make the final concentration of the metal salt in the sample at 20 mM or more.

However, as the final concentration of the metal salt in the sample excessively increases, the reactivity of the *Limulus* reagent to Et tends to decrease. Thus, when Elimination method 1 of the present invention is used in the Et-assay method of the present invention as described later, the final concentration of the metal salt in the sample can be determined with the balance between the "elimination of the reactivity of LAM to the *Limulus* reagent" and the "retention of the reactivity of the *Limulus* reagent to Et". For example, if the former is considered to be more important than the latter, the concentration of the metal salt in the sample is desirably enhanced even if the latter is sacrificed in any way. If the latter is considered to be more important than the former, the concentration of the metal salt in the sample is preferably kept low level. For eliminating the reactivity of LAM to the *Limulus* reagent while maintaining the reactivity of the *Limulus* reagent to Et, the metal salt is allowed to coexist with the sample to make the final concentration of the metal salt in the sample preferably in the range of 20 to 500 mM, more preferably in the range of 30 to 500 mM. It is also preferable to allow the metal salt to coexist with the sample so that the final concentration of the metal salt in the sample is in the range of 30 to 300 mM.

Further, for example, when sodium sulfate is used as a metal salt, sodium sulfate is allowed to coexist with the sample to make the final concentration of sodium sulfate in the sample preferably in the range of 30 to 200 mM, more preferably in the range of 30 to 100 mM, still more preferably in the range of 40 to 80 mM, particularly preferably in the range of 50 to 70 mM, particularly preferably about 60 mM. In addition, when sodium chloride is used as a metal salt, sodium chloride is allowed to coexist with the sample to make the final concentration of sodium chloride in the sample preferably in the range of 150 to 500 mM, more preferably in the range of 200 to 400 mM, particularly preferably in the range of 250 to 350 mM. Further, when magnesium sulfate is used as a meal salt, magnesium sulfate is allowed to coexist with the sample to make the final concentration of magnesium sulfate in the sample preferably in the range of 80 to 300 mM, more preferably in the range of 100 to 200 mM. Further, when potassium sulfate is used as a metal salt, potassium sulfate is allowed to coexist with the sample to make the final concentration of potassium sulfate in the sample preferably in the range of 50 to 200 mM, more preferably in the range of 50 to 150 mM. In addition, when magnesium chloride is used as a metal salt, magnesium chloride is allowed to coexist with the sample to make the final concentration of magnesium chloride in the sample preferably in the range of 80 to 300 mM, more preferably in the range of 100 to 250 mM. Further, when potassium chloride is used as a metal salt, potassium chloride is allowed to coexist with the sample to make the final concentration of potassium chloride in the sample preferably in the range of 200 to 500 mM, more preferably in the range of 200 to 300 mM. Further, when sodium nitrate is used as a metal salt, sodium nitrate is allowed to coexist with the sample to make the final concentration of sodium nitrate in the sample preferably in the range of 150 to 400 mM, more preferably in the range of 200 to 300 mM. Further, when potassium nitrate is used as a metal salt, potassium nitrate is allowed to coexist with the sample to make the final concentration of potassium nitrate in the sample preferably in the range of 150 to 400 mM, more preferably 180 to 300 mM. Further, when calcium chloride is used as a metal salt, calcium chloride is allowed to coexist with the sample to make the final concentration of calcium chloride in the sample preferably in the range of 100 to 300 mM, more preferably 130 to 200 mM.

Further, as described above, the final concentration of the metal salt in the sample can be also suitably determined with reference to the degree of eliminating the reactivity of LAM to be desired by a person who carries out Elimination method 1 of the present invention. Specifically, the final concentration of the metal salt is selected so that the relative activity of LAM will be preferably 20% or less, more preferably 10% or less, particularly preferably 5% or less, particularly preferably 1% or less.

Further, the term "relative activity of LAM" in Elimination method 1 of the present invention means a percentage (%) calculated by dividing the reactivity level of LAM to the Limulus reagent when any metal salt is allowed to coexist with the sample to attain a certain final concentration thereof by the reactivity level of LAM to the Limulus reagent when the metal salt is not allowed to coexist with the sample. Specifically, the percentage can be calculated by the method described in Examples, so the method can be referred.

Further, in the elimination method of the present invention, the Limulus reagent is not particularly limited as long as it is a reagent containing an amoebocyte lysate of a horseshoe crab as a main component. The horseshoe crab species to be used include, but not limited to, Limulus polyphemus (North American horseshoe crab), and Tachypleus tridentatus, and Tachypleus gigas, Tachypleus rotundicauda (all of them are Asian horseshoe crabs). An amoebocyte lysate of any one of them can be used. The amoebocyte lysate can be produced by a method known in the art (for example, a method in which distilled water is added to the horseshoe crab amoebocyte and then the whole is gently swirled around overnight on a shaking table at 4° C. to break down the amoebocyte, and a supernatant thereof is used, or a method in which a 0.02 M tris-HCl buffer (pH 8.0) is added to the horseshoe crab amoebocyte, the whole is uniformly broken with a homogenizer and extracted, and a supernatant thereof is used). Alternatively, any Limulus reagent commercially available may be used. Such a Limulus reagent may be reactive to both Et and BG. A preferable Limulus reagent is prepared so that it does not react with BG (such a reagent is herein referred to as an "Et-specific Limulus reagent"). The Et-specific Limulus reagent can be produced by a method known in the art (for example, a method involving allowing aprotinin to coexist with a Limulus reagent, a method involving allowing alkyl glycoside to coexist with a Limulus reagent, or a method involving allowing a polycarboxylic acid derivative or glyceryl derivative of (1→3)-β-D-glucans to coexist with a Limulus reagent). Alternatively, one commercially available (for example, Endospacy ES-50M (Seikagaku Kogyo Co., Ltd.)) may be used as the Et-specific Limulus reagent. The Et-specific Limulus reagent may be, for example, contains, as a main component or a main constituent, an amoebocyte lysate containing a substance that inhibits a Limulus reaction in the presence of a G factor such as a G-factor activation inhibitor or an anti-G-factor antibody.

Elimination method 1 of the present invention may further include the step of preparing an LAM-containing sample, the step of allowing the LAM-containing sample to coexist with components other than a metal salt, or the step of evaluating whether the reactivity of LAM to a Limulus reagent is eliminated, in addition to the step of allowing the LAM-containing sample to coexist with the metal salt. Components other than the metal salt include a surfactant, an antituberculous antibody, an anti-LAM antibody, BG, carboxymethylated BG, a strong alkaline substance, Polymyxin B, colistin, concanavalin A, histidine, and histamine. Carrying out the step of allowing the LAM-containing sample to coexist with those components is preferable because an additionally excellent eliminating effect on the reactivity of LAM to a Limulus reagent can be expected. Further, the step of allowing the LAM-containing sample to coexist with, for example, the Limulus reagent as a component other than the above metal salt may be carried out to permit the application of Elimination method 1 of the present invention to an Et-specific assay. For the Et-specific assay, "<3> Et-assay method of the present invention" as described later can be referred.

Further, the expression "eliminate the reactivity" is used in the description as a term to mean not only the complete elimination of the reactivity but also the partial elimination of the reactivity (a decrease or reduction in reactivity).

Elimination method 1 of the present invention as described above can be applied to a method of assaying Et in a condition where the influence of LAM is eliminated or reduced. For details, the Et-assay method of the present invention as described later is referable.

<2> Elimination Method 2 of the Present Invention

Elimination method 2 of the present invention is a method of eliminating the reactivity of LAM in an LAM-containing sample to a Limulus reagent, comprising at least the step of allowing the sample to coexist with a buffer.

In Elimination method 2 of the present invention, the concentration (concentration after the coexistence) of the buffer in the LAM-containing sample in the step of allowing the sample to coexist with the buffer (hereinafter, simply described as the "final concentration of the buffer in the sample") is not particularly limited as long as such a concentration can exert an action of eliminating the reactivity of LAM in the LAM-containing sample to a Limulus reagent. A person skilled in the art can appropriately define the final concentration of the buffer depending on, for example, the type of the buffer to be used and the degree of the above-mentioned eliminating effect on the reactivity to be desired by a person who carries out Elimination method 2 of the present invention. The buffer is allowed to coexist with the sample to make the final concentration preferably in the range of 100 to 300 mM, more preferably in the range of 150 to 200 mM, particularly preferably about 200 mM.

The "LAM-containing sample" and the "Limulus reagent" can be explained just as in the case of "<1> Elimination method 1 of the present invention" as described above.

Further, in Elimination method 2 of the present invention, the buffer has only to have a function of eliminating the reactivity of LAM in an LAM-containing sample to a Limulus reagent. The types, number, combination, and so on of buffers to be used are not particularly limited. The buffer may be of a single type or may be a combination of two or more types. For example, a mixture of two or more types of buffers may be used. In addition, the buffer is not limited by, for example, the state or form in which the buffer exists. For example, the buffer may be in a solid state to be powderized or in a state of solution such as one dissolved in purified water. Further, the buffer may be present in mixture with any one of the components other than the buffer including a surfactant, an antituberculous antibody, an anti-LAM antibody, BG, carboxymethylated BG, a strong alkaline substance, Polymyxin B, colistin, concanavalin A, histidine, histamine, and a Limulus reagent. Here, for example, when the buffer is present in mixture with any one of the substances such as a surfactant, an antituberculous antibody, an anti-LAM antibody, BG, carboxymethylated BG, a strong alkaline substance, Polymyxin B, colistin, concanavalin A, histidine, and histamine, a more preferable eliminating effect on reactivity of LAM to a *Limulus* reagent can be expected. For example, when the buffer is present in mixture with a *Limulus* reagent and LAM-containing sample contains Et or may contain Et, Et in the above-mentioned sample can be specifically assayed by detecting or measuring the *Limulus* reaction initiated by Et in the LAM-containing sample after allowing the sample to coexist with a mixture of the *Limulus* reagent and the buffer. For more specific description about the assay method, "<3> Et-assay method of the present invention" described later can be referred.

Specific examples of the buffer preferably include tris(hydroxymethyl)aminomethane (hereinafter, also referred to as "Tris"), 2-[4-(2-hydroxyethyl)-1-piperazinyl]ethanesulfonic acid (hereinafter, also referred to as "HEPES"), N-tris(hydroxymethyl)methyl-2-aminoethanesulfonic acid (hereinafter, also referred to as "TES"), 2-hydroxy-3-[4-(2-hydroxyethyl)-1-piperazinyl]propanesulfonic acid monohydrate (hereinafter, also referred to as "HEPPSO"), N-[tris(hydroxymethyl)methyl]glycine (hereinafter, also referred to as "Tricine"), N,N-bis(2-hydroxyethyl)glycine (hereinafter, also referred to as "Bicine"), and imidazole (hereinafter, also referred to as "Imidazole").

Elimination method 2 of the present invention may further include, for example, the step of preparing an LAM-containing sample, the step of allowing the LAM-containing sample to coexist with components other than the buffer, or the step of evaluating whether the reactivity of LAM to a *Limulus* reagent is eliminated, in addition to the step of allowing the LAM-containing sample to coexist with the buffer. Components other than the buffer include a surfactant, an anti-tuberculous antibody, an anti-LAM antibody, BG, carboxymethylated BG, a strong alkaline substance, Polymyxin B, colistin, concanavalin A, histidine, and histamine. Carrying out the step of allowing the LAM-containing sample to coexist with those components is preferable because an additionally excellent eliminating effect on the reactivity of LAM to a *Limulus* reagent can be expected. Further, for example, the step of allowing the LAM-containing sample to coexist with the *Limulus* reagent as a component other than the buffer may be carried out to permit the application of Elimination method 2 of the present invention to an Et-specific assay. For the Et-specific assay, "<3> Et-assay method of the present invention" as described later can be referred.

Further, any one of the metal salts such as sulfates such as sodium sulfates, magnesium sulfate, and potassium sulfate; metal chlorides such as sodium chloride, magnesium chloride, potassium chloride, and calcium chloride; and nitrates such as sodium nitrate and potassium nitrate as described in the above "<1> Elimination method 1 of the present invention" may be allowed to coexist with an LAM-containing sample and used together with the buffer as an additional substance other than the buffer, thereby an excellent effect is expected, which means that an excellent effect is expected by combining the elimination methods 1 and 2 of the present invention.

Elimination method 2 of the present invention as described above can be applied to a method of assaying Et in a condition where the influence of LAM is eliminated or reduced. For details, the Et-assay method of the present invention as described later is referable.

<3> Et-Assay Method of the Present Invention

Et-assay method of the present invention is a method of assaying Et in a sample containing LAM and Et by the use of a *Limulus* reagent. The method includes at least the step of eliminating the reactivity of LAM to the *Limulus* reagent by Elimination method 1 or 2 of the present invention.

The Et-assay method is a method in which the above Elimination method 1 or 2 of the present invention is applied to a method of assaying Et. Thus, the "LAM-containing sample" and the "*Limulus* reagent" can be explained just as in the case of "<1> Elimination method 1 of the present invention" and "<2> Elimination method 2 of the present invention" as described above. The *Limulus* reagent is also preferably an Et-specific *Limulus* reagent. The sample to be used contains or may contain Et in addition to LAM. The term "Et-containing sample" as used herein means one which contains or may contain Et.

Further, in the Et-assay method, the phrase "the reactivity of LAM to a *Limulus* reagent is eliminated by Elimination method 1 or 2 of the present invention" means that either Elimination method 1 or 2 may be used for eliminating the reactivity of LAM to the *Limulus* reagent, or a combination of both methods may be used for the elimination.

In the case of eliminating the reactivity of LAM to a *Limulus* reagent by Elimination method 1 of the present invention, the metal salt and the final concentration of the metal salt in the sample can be explained just as in the case of "<1> Elimination method 1 of the present invention" as described above. In the case of eliminating the reactivity of LAM to a *Limulus* reagent by the Elimination method 2 of the present invention, the buffer and the final concentration of the buffer in the sample can be explained just as in the case of "<2> Elimination method 2 of the present invention" as described above.

In the Et-assay method, the reactivity of LAM to a *Limulus* reagent may be eliminated by Elimination method 1 of the present invention. In this case, from a standpoint of the balance between the "elimination of the reactivity of LAM to the *Limulus* reagent" and the "retention of the reactivity of the *Limulus* reagent to Et" as described in the above "<1> Elimination method 1 of the present invention", a person skilled in the art can suitably determine the final concentration of the metal salt in the sample depending on the degree of the retention of the reactivity of the *Limulus* reagent to Et desired by a person who carries out the Et-assay method. Specifically, the final concentration of the metal salt in the sample is selected so that the relative activity of Et will be preferably 50% or more, more preferably 65% or more, particularly preferably 80% or more. By the way, the relative activity of Et is calculated by replacing the LAM in the "relative activity of LAM" with Et. Specifically, the relative activity will be referred by Examples.

The assay of Et by the Et-assay method can be performed by carrying out the detection or assay of a *Limulus* reaction caused by Et after or simultaneous with the elimination of the reactivity of LAM to the *Limulus* reagent by Elimination method 1 or 2 of the present invention. Further, the Et-assay method may include another step in addition to the above-mentioned steps.

The timing of eliminating the reactivity of LAM to a *Limulus* reagent by Elimination method 1 or 2 of the present invention is not particularly limited either. For instance, the following procedure can be performed: the sample is allowed to coexist with a metal salt or a buffer in advance so that the reactivity of LAM to a *Limulus* reagent is eliminated, followed by contacting the sample with the *Limulus* reagent. Alternatively, the following procedure can be performed: a

*Limulus* reagent is mixed with a metal salt or a buffer in advance and the sample is then contacted with the mixture, thereby eliminating the reactivity of LAM to the *Limulus* reagent while carrying out a *Limulus* reaction.

The Et-assay method provides a method of assaying Et as follows.

A method of assaying Et, comprising at least the following steps (a) and (b):

(a) allowing a sample containing Et and LAM to coexist with a metal salt or a buffer; and (b) contacting the sample with a *Limulus* reagent to detect a *Limulus* reaction initiated by Et after the coexistence.

In the above step (a), either the metal salt or the buffer may coexist with the sample containing Et and LAM, or both the metal salt and the buffer may coexist with the sample.

Further, the Et-assay method also provides a method of assaying Et as follows.

A method of assaying Et, comprising at least the following steps (a) and (b):

(a) allowing a *Limulus* reagent to coexist with a metal salt or a buffer; and (b) contacting a sample containing Et and LAM with the *Limulus* reagent to detect a *Limulus* reaction initiated by Et after the coexistence.

In the above step (a), either the metal salt or the buffer may coexist with the *Limulus* reagent, or both the metal salt and the buffer may coexist with the reagent.

The *Limulus* reaction induced by Et can be detected by a conventionally known method. For example, conventionally known methods such as colorimetric assay (endpoint assay or kinetic assay), gel-clot assay, and turbidimetric assay (endpoint assay or kinetic assay) described in, for example, Pharmacopeia of Japan can each be employed as the detecting methods corresponding to respective methods.

The "measurement" as used in the description is a general idea which includes not only quantitative measurement but also qualitative measurement (measurement of the presence or absence of Et, etc.).

Various methods can be employed as the quantitative measurement of Et depending on the object. For example, strict determination can be carried out by: preparing a calibration curve or a relational expression on a relationship between the Et concentration and the strength of *Limulus* reaction using a sample having an already known Et concentration; and using the curve or the expression. In addition, when strict determination is not necessary, amounts of Et between two or more samples may be compared. Since Et induces a *Limulus* reaction, the amount of Et in a sample is large when the strength of the *Limulus* reaction is high.

Et can be qualitatively measured by detecting the presence or absence of the *Limulus* reaction. Since Et induces a *Limulus* reaction, Et is present in a sample when the *Limulus* reaction is detected.

According to the Et-assay method, the reactivity of LAM in an LAM-containing sample to a *Limulus* reagent can be eliminated. Thus, Et in the sample can be assayed without any influence of LAM or with a reduced influence of LAM.

<4> Disease Detection Method of the Present Invention

Disease detection method of the present invention is a method of detecting an Et-associated disease, comprising using the Et-assay method of the present invention.

Disease detection method of the present invention is the application of the Et-assay method to the detection of an Et-associated disease. In the disease detection method, a sample originating from a living body which contains or may contain Et is used as an "LAM-containing sample" in the Et-assay method. The "sample originating from the living body" can be explained just as in the case of "<1> Elimination method 1 of the present invention" as described above.

When blood is used as the "sample originating from the living body", as in the case of "<1> Elimination method 1 of the present invention", it is preferable to remove or inactivate *Limulus* reaction inhibitors in blood (serine protease, serine protease inhibitor, etc.) in advance by a conventionally known method (e.g., the method described in JP-A-58-85162).

The Et-associated diseases as detection targets are not specifically limited as long as they are Et-induced diseases. The diseases include endotoxemia, sapraemia, and gram-negative infection diseases.

The "detection" in the disease detection method of the present invention is a general idea which includes not only qualitative detection (detection of the presence or absence of an Et-associated disease) but also quantitative measurement (detection of the malignancy of an Et-associated disease, etc.).

The qualitative detection of an Et-associated disease can be performed by applying a qualitative assay of Et. The qualitative assay of Et can be referred by "<3> Et-assay method of the present invention" as described above. If a *Limulus* reaction is detected, then the presence of Et in the sample is confirmed. As a result, the sample may be of an Et-associated disease or may be suspected thereof.

The quantitative detection of an Et-associated disease can be performed by applying a quantitative assay of Et. The quantitative assay of Et can be referred by "<3> Et-assay method of the present invention" as described above. Et induces a *Limulus* reaction. Thus, the stronger the *Limulus* reaction, the more the content of Et in the sample. Accordingly, the intensity of the *Limulus* reaction can be correlated with a high malignancy of the Et-associated disease or suspicion thereof.

<5> Kit for Assaying Et of the Present Invention.

A kit for assaying Et of the present invention includes a *Limulus* reagent, and a metal salt or a buffer as components; and is used in an assay of Et with a decreased influence of LAM.

The use of the Et-assay kit allows the Et-assay method to be simply carried out.

In the Et-assay kit, the term "assay of Et with a decreased influence of LAM" means that the assay of Et is carried out without any influence of LAM or with a deceased influence of LAM by eliminating the reactivity of LAM to a *Limulus* reagent. Here, the degree of eliminating the reactivity of LAM to the *Limulus* reagent is not particularly limited. For example, the reactivity of LAM is eliminated so that the relative activity of LAM will be preferably 50% or less, more preferably 20% or less, still more preferably 10% or less, particularly preferably 5% or less.

The term "*Limulus* reagent" can be explained just as in the case of "<1> Elimination method 1 of the present invention" as described above. Therefore, the *Limulus* reagent is preferably an Et-specific *Limulus* reagent.

Further, the term "metal salt" can be explained just as in the case of "<3> Et-assay method of the present invention" as described above. Therefore, specific preferable metal salts include: sulfates such as sodium sulfate, magnesium sulfate, and potassium sulfate; metal chlorides such as sodium chloride, magnesium chloride, potassium chloride, and calcium chloride; and nitrates such as sodium nitrate and potassium nitrate.

In addition, the term "buffer" can be also explained in a manner similar to that of "<3> Et-assay method of the present invention". Therefore, specific preferable buffers include Tris, HEPES, TES, HEPPSO, Tricine, Bicine, and Imidazole.

The Et-assay kit is not particularly limited as long as it includes at least a *Limulus* reagent, and a metal salt or a buffer as components. Here, the phrase "includes at least a *Limulus* reagent, and a metal salt or a buffer as components" means that either the metal salt or the buffer may be included as a component in addition to the *Limulus* reagent or both of them may be included as components. In addition, the kit for assaying Et of the present invention may further include another component in addition to the above components. Examples of another component include distilled water for a blank test, a dissolving solution for a reaction reagent, a reaction buffer, an Et-standard substance, and a reaction substrate. Further, the Et-assay kit may also include a positive control (QC control) for keeping the practical levels of the respective assay batches at certain levels, for example.

Those components may be independently contained and stored in different containers, respectively. The kit of the present invention preferably includes an instruction manual that describes the usage of the kit and the fact that a metal salt or a buffer in the kit is used for eliminating the reactivity of LAM in a sample to a *Limulus* reagent.

The assay of Et with the Et-assay kit can be carried out in accordance with "<3> Et-assay method of the present invention".

<6> Kit for Diagnosing Disease of the Present Invention

A kit for diagnosing a disease of the present invention is a kit for diagnosing an Et-associated disease, composed of the Et-assay kit.

The use of the kit for diagnosing a disease of the present invention allows the diagnosis of an Et-associated disease to be simply carried out.

The Et-associated disease as a diagnostic target is not particularly limited as long as it is an Et-induced disease. Examples of the disease include endotoxemia, sapraemia, and gram-negative infection diseases. In addition, the "sample originating from the living body" to be used can be explained just as in the case of "<4> Disease detection method of the present invention" as described above. In other words, the "sample originating from the living body" to be used is preferably blood. In addition, when the blood is used as the "sample originating from the living body", the elimination or inactivation of *Limulus* reaction inhibitors (such as serine protease and serine protease inhibitor) in blood in advance is preferable just as in the case of the above <4>.

The application of the above "<4> Disease detection method of the present invention" allows the diagnosis of an Et-associated disease with the kit for diagnosing a disease of the present invention to be carried out.

<7> Reactivity-eliminating Agent 1 of the Present Invention

Reactivity-eliminating agent 1 of the present invention contains a metal salt as an active ingredient; and is used for eliminating the reactivity of LAM to a *Limulus* reagent.

The terms "metal salt", "*Limulus* reagent", and "eliminates the reactivity" can be referenced to the description thereof in the above "<1> Elimination method 1 of the present invention".

<8> Reactivity-eliminating Agent 2 of the Present Invention

Reactivity-eliminating agent 2 of the present invention contains a buffer as an active ingredient; and is used for eliminating the reactivity of LAM to a *Limulus* reagent.

The terms "buffer", "*Limulus* reagent", and "eliminates the reactivity" can be referenced to the description thereof in the above "<2> Elimination method 2 of the present invention".

EXAMPLES

Hereinafter, the present invention will be described with reference to examples. However, the present invention is not restricted by the following examples.

1. Comparison Between Reactivities of LAM and Et to *Limulus* Reagent in the Presence of Sodium Sulfate—Part 1

LAM and Et were compared with each other with respect to their reactivities to a *Limulus* reagent containing sodium sulfate as a metal salt. Hereinafter, an amoebocyte lysate (component extracted from the blood cell of a horseshoe crab) will be referred to as a "lysate". In addition, LAM used in this example is LAM isolated and purified at high purity by organic solvent extraction and column chromatography from dead cells of *Mycobacterium tuberculosis* Aoyama-B strain (commercially available from Nacalai Tesque, Inc.).

1-1. Example in which Lysate Originating from *Tachypleus tridentatus* is Used

Sodium sulfate, Tris-HCl buffer (pH 8.0), magnesium sulfate, chromogenic substrate (Boc-Leu-Gly-Arg-pNA (paranitroaniline) hydrochloride) (manufactured by Peptide Institute, Inc.), and lysate originating from *Tachypleus tridentatus* were added to an Et- and BG-free microtiter plate (Toxipet plate LP, Seikagaku Corporation) so that the concentrations (mM) or use amounts of these components will be 0, 10, 20, 30, 40, or 50 mM of sodium sulfate, 50 mM of Tris-HCl buffer (pH 8.0), 20 mM of magnesium sulfate, 0.167 mM of the chromogenic substrate (Boc-Leu-Gly-Arg-pNA hydrochloride), and 20 μL of the lysate originating from *Tachypleus tridentatus* in 200 mL of a reaction solution. The plate was added with 25 μL of 100 ng/mL LAM and 25 μL of 1 ng/mL Et (manufactured by Difco Co., Ltd., originating from *E. coli* 0111, strain B4), followed by the reaction for 30 minutes in a microplate reader (Well Reader SK603, Seikagaku Corporation). The rate of absorbance change per minute (mAbs/min) [A 405 nm-492 nm (control wavelength)] was automatically measured. The values obtained by the respective measurements were compared with a value obtained when the concentration of sodium sulfate was 0 mM (control value; assumed 100%), thereby the relative activity (%) of LAM and the relative activity (%) of Et was calculated. The results are shown in FIG. 1 and FIG. 2.

Figure 2:
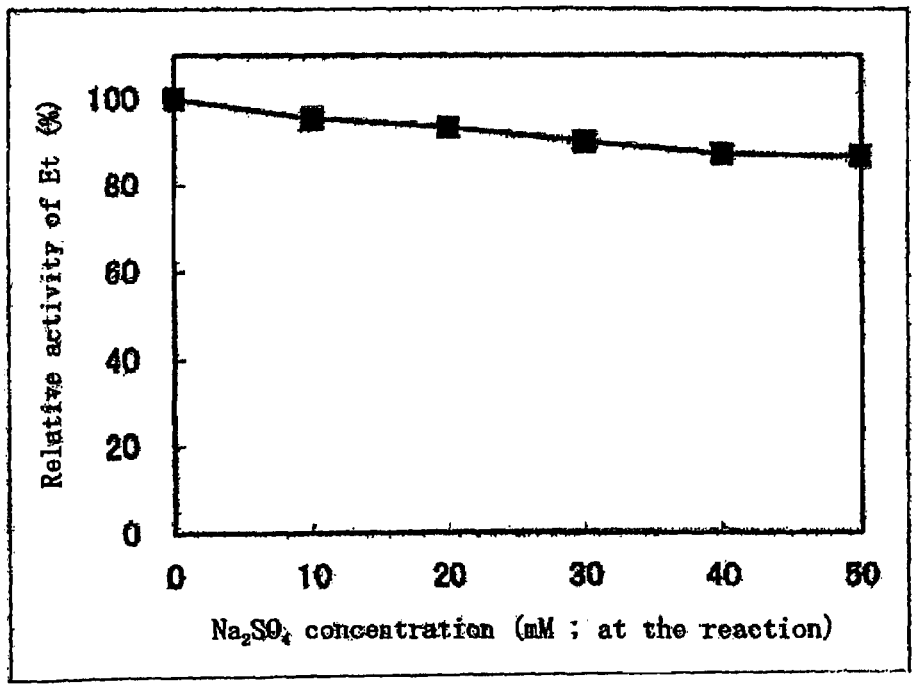
FIG. 2 is a diagram showing the relationship between the concentration of sodium sulfate and the relative activity of Et in a *Limulus* reaction with a lysate originating from *Tachypleus tridentatus*.

When the concentration of sodium sulfate was 50 mM, the relative activity of LAM to the *Limulus* reagent was almost completely inhibited as the relative activity showed 0.3% (i.e., the reactivity of LAM was eliminated by 99.7%) (FIG. 1). On the other hand, at this concentration, Et showed a relative activity of 86.6%. The reactivity of Et to the *Limulus* reagent was found to be dominantly retained as compared with that of LAM (FIG. 2).

1-2. Example in which Lysate Originating from *Limulus polyphemus* is Used

An examination was carried out in a manner similar to that of the above section 1-1 except that: a lysate originating from *Limulus polyphemus* was used instead of the lysate originating from *Tachypleus tridentatus* used in the above section 1-1; the concentration of LAM was 1,000 ng/mL; and the concentration of Et was 2 ng/mL. The results are shown in FIG. 3 and FIG. 4.

When the concentration of sodium sulfate was 50 mM, the reactivity of LAM to the *Limulus* reagent was almost completely inhibited as the relative activity of LAM showed 0.9%

Figure 3:
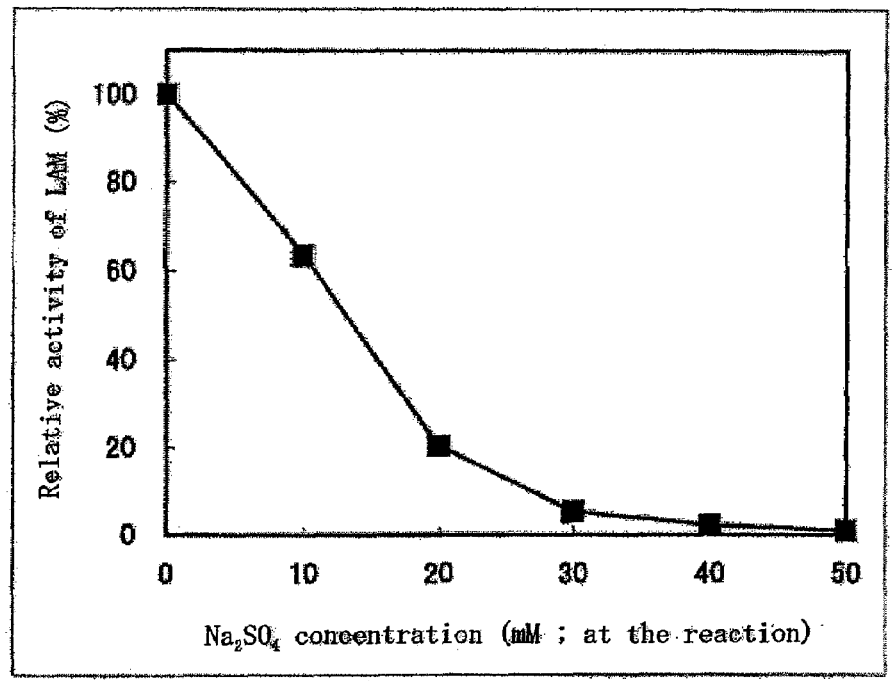
FIG. 3 is a diagram showing a relationship between the concentration of sodium sulfate and the relative activity of LAM in a *Limulus* reaction with a lysate originating from *Limulus polyphemus*.
Figure 4:
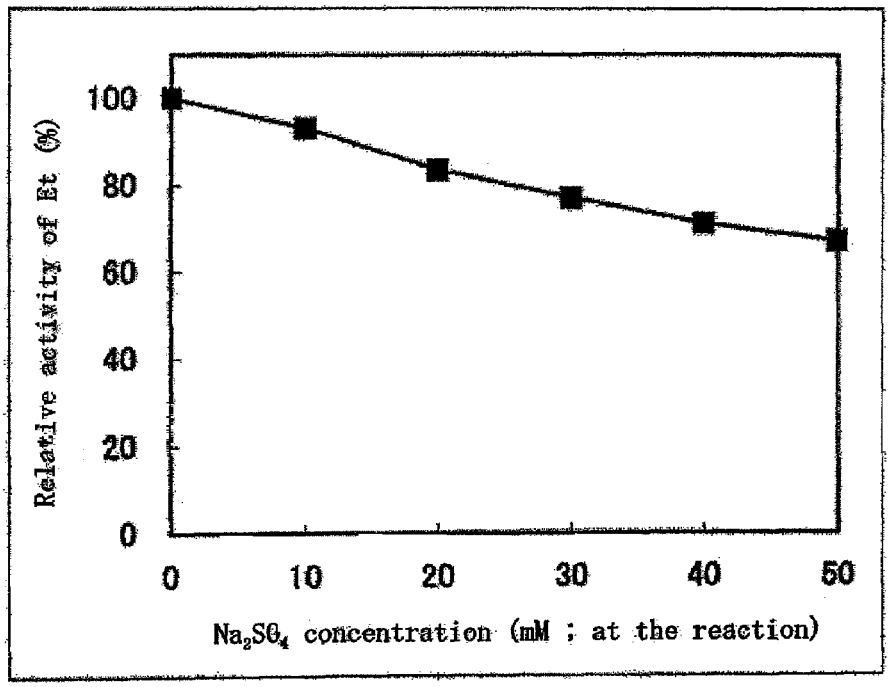
FIG. 4 is a diagram showing the relationship between the concentration of sodium sulfate and the relative activity of Et in a *Limulus* reaction with a lysate originating from *Limulus polyphemus*.

(FIG. 3). On the other hand, at this concentration, Et showed a relative activity of 67.3%. The reactivity of Et to the *Limulus* reagent was found to be dominantly retained as compared with that of LAM (FIG. 4).

2. Comparison Between Reactivities of LAM and Et to Et-Specific *Limulus* Reagent in the Presence of Sodium Sulfate—Part 2

LAM and Et were compared with each other with respect to their reactivities to an Et-specific *Limulus* reagent containing sodium sulfate as a metal salt. The Et-specific *Limulus* reagent used was Endospacy ES-50M (Seikagaku Corporation). In addition, LAM and Et were the same as those used in Example 1 described above.

Sodium sulfate was added to a microtiter plate (Toxipet plate LP, Seikagaku Corporation) so that the concentration thereof in 100 μL of a reaction solution will be 0, 15, 30, 60, 90, or 120 mM. The plate was added with 25 μL of 20 μg/mL LAM or 25 μL of 0.4 ng/mL Et, and 50 μL of a base compound dissolved by a buffer provided in Endospacy ES-50M. The plate was subjected to a reaction for 30 minutes in a microplate reader (Well Reader SK603, Seikagaku Corporation). The rate of absorbance change per minute (mAbs/min) [A 405 nm-492 nm (control wavelength)] was automatically measured. The relative activity (%) of LAM and the relative activity (%) of Et were obtained in a manner similar to Example 1 as described above. The results are shown in FIG. 5 and FIG. 6.

Figure 5:
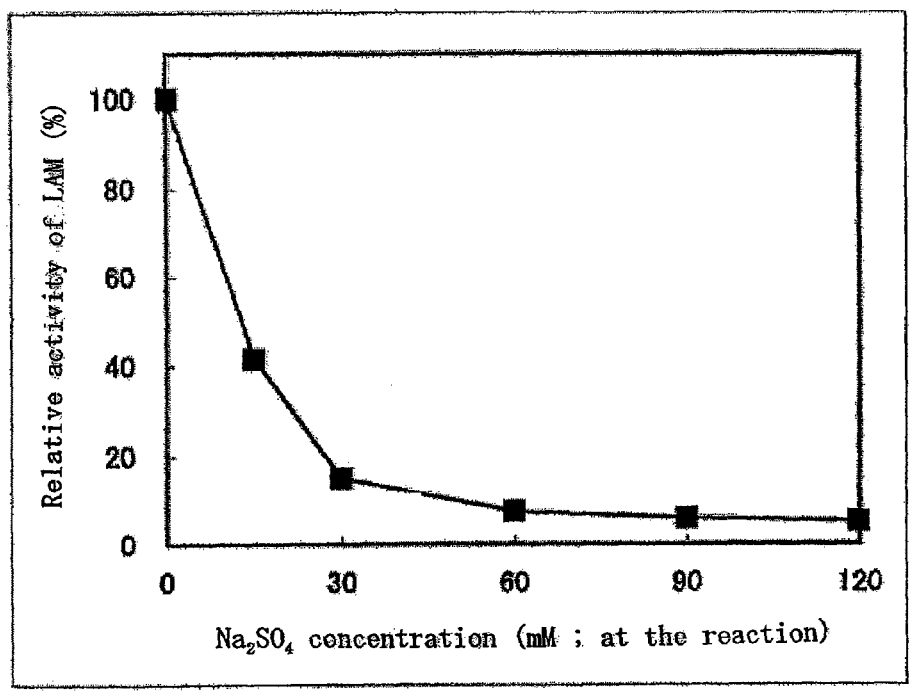
FIG. 5 is a diagram showing a relationship between the concentration of sodium sulfate and the relative activity of LAM in a *Limulus* reaction with an Et-specific *Limulus* reagent.
Figure 6:
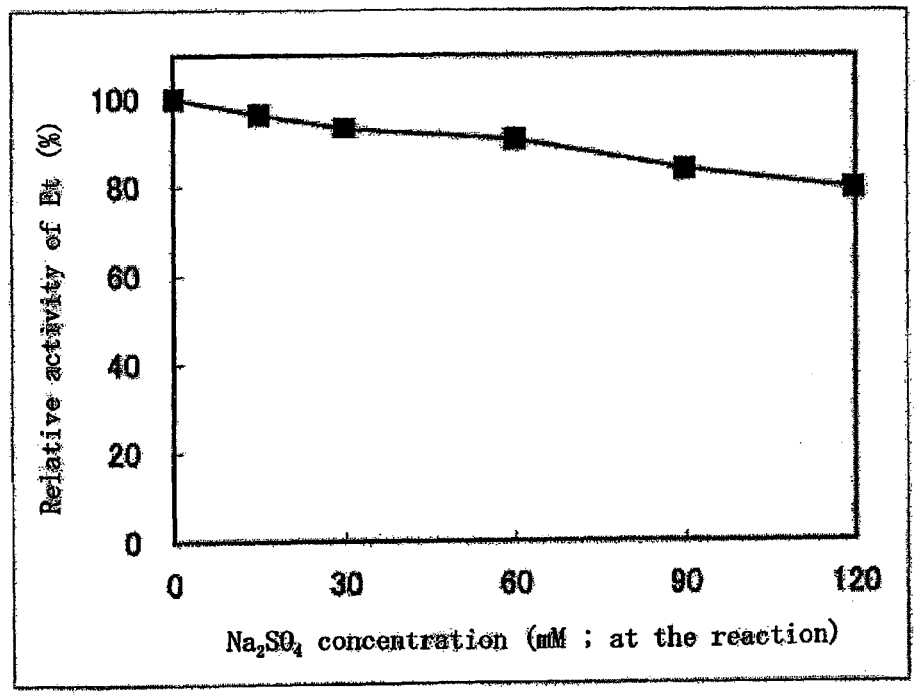
FIG. 6 is a diagram showing the relationship between the concentration of sodium sulfate and the relative activity of Et in a *Limulus* reaction with an Et-specific *Limulus* reagent.

When the concentration of sodium sulfate was 120 mM, the reactivity of LAM to the Et-specific *Limulus* reagent was significantly inhibited as the relative activity of LAM showed 5.2% (FIG. 5). On the other hand, at this concentration, Et showed a relative activity of 79.8%. The reactivity of Et to Et-specific *Limulus* reagent was found to be dominantly retained as compared with that of LAM (FIG. 6).

3. Comparison Between Reactivities of LAM and Et to Et-Specific *Limulus* Reagent in the Presence of Sodium Chloride An examination was carried out in a manner similar to Example 2 as described above except that sodium chloride was used instead of sodium sulfate. In this case, sodium chloride was added to a microtiter plate (Toxipet plate LP, Seikagaku Corporation) so that the concentration thereof in 100 μL of a reaction solution will be 0, 50, 100, 150, 200, or 250 mM. The results are shown in FIG. 7 and FIG. 8.

Figure 7:
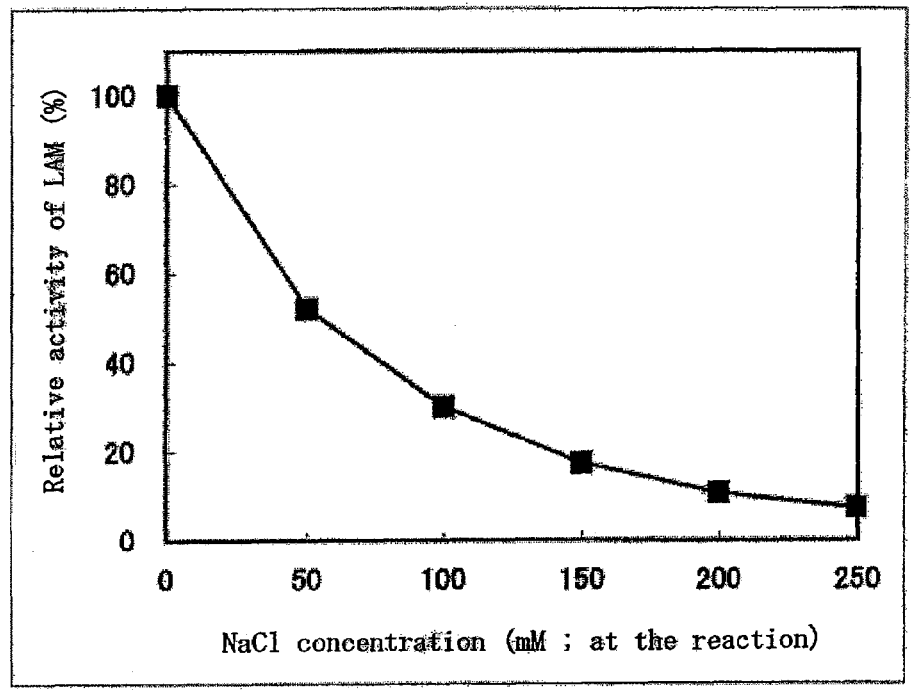
FIG. 7 is a diagram showing a relationship between the concentration of sodium chloride and the relative activity of LAM in a *Limulus* reaction with an Et-specific *Limulus* reagent.
Figure 8:
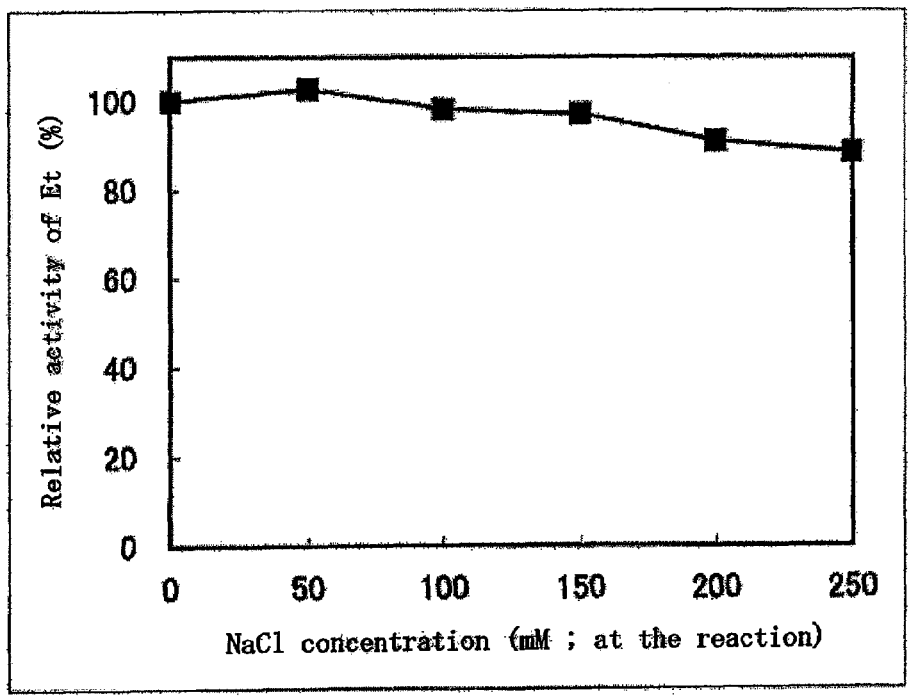
FIG. 8 is a diagram showing the relationship between the concentration of sodium chloride and the relative activity of Et in a *Limulus* reaction with an Et-specific *Limulus* reagent.

When the concentration of sodium chloride was 250 mM, the reactivity of LAM to the Et-specific *Limulus* reagent was significantly inhibited as the relative activity of LAM showed 7.2% (FIG. 7). On the other hand, at this concentration, Et showed a relative activity of 88.3%. The reactivity of Et to the Et-specific *Limulus* reagent was found to be dominantly retained as compared with that of LAM (FIG. 8).

4. LAM-complete Inhibition Concentrations of Respective Metal Salts and Relative Activity of Et at the Concentrations Various kinds of metal salts shown in Table 1 were used and the same operations as those of Example 1-1 and Example 1-2 described above were carried out. Subsequently, a change in relative activity (%) of LAM in response to a change in concentration of a metal salt in the reaction was investigated, and the concentrations of the metal salts when the relative activity (%) of LAM almost completely disappeared (hereinafter, referred to as "LAM-complete inhibition concentration") were calculated. The relative activities (%) of Et in the presence of the LAM-complete inhibition concentrations of metal salts were determined by the same operations as those of Example 1-1 and Example 1-2. The results are shown in Table 1.

TABLE 1

LAM-complete inhibition concentrations and relative activities of Et in the presence of various metal salts

| Lysate used | Metal salt | LAM-complete inhibition concentration | Relative activity of Et |
|---|---|---|---|
| LAL-lysate | Sodium sulfate | About 50 mM | → 67-53% (3Lot) |
| | Magnesium sulfate | About 170 mM | → 14-5% (3Lot) |
| | Potassium sulfate | About 100 mM | → 31% (1Lot) |
| | Sodium chloride | 250 mM (or more) | → 57-46% (3Lot) |
| | Magnesium chloride | About 200 mM | → 9% (1Lot) |
| | Potassium chloride | 250 mM (or more) | → 36-17% (3Lot) |
| | Sodium nitrate | About 250 mM | → 34% (1Lot) |
| | Potassium nitrate | About 250 mM | → 23% (1Lot) |
| | Calcium chloride | About 160 mM | → 4% (1Lot) |
| TAL-lysate | Sodium sulfate | About 50 mM | → 87-74% (3Lot) |
| | Magnesium sulfate | About 110 mM | → 78-64% (3Lot) |
| | Potassium sulfate | About 60 mM | → 71% (1Lot) |
| | Sodium chloride | About 250 mM | → 95-72% (3Lot) |
| | Magnesium chloride | About 120 mM | → 61% (1Lot) |
| | Potassium chloride | 250 mM (or more) | → 90-64% (3Lot) |
| | Sodium nitrate | About 250 mM | → 89% (1Lot) |
| | Potassium nitrate | About 200 mM | → 91% (1Lot) |
| | Calcium chloride | About 160 mM | → 17% (1Lot) |

(Note)
Assay was performed in a reaction solution amount of 200 μL.

For each metal salt, the measurements were carried out for the number of times corresponding to the lot number shown in the parenthesis of the list, and the LAM-complete inhibition concentrations and the relative activities of Et were calculated.

Further, in the above table, the LAL-lysate means a lysate originating from *Limulus polyphemus* and the TAL-lysate means a lysate originating from *Tachypleus tridentatus*.

5. Comparison Between Reactivities of LAM and Et to *Limulus* Reagent in the Presence of Tris Buffer LAM and Et were compared with respect to their reactivities to a *Limulus* reagent by using Tris buffer as a buffer.

5-1. Example in which Lysate Originating from *Tachypleus tridentatus* is Used

Tris-HCl buffer (pH 8.0), magnesium sulfate, a chromogenic substrate, and a lysate originating from *Tachypleus tridentatus* were added to Toxipet plate LP so that the concentrations (mM) or use amounts of these components will be 25, 50, 100, 150, or 200 mM of the Tris-HCl buffer (pH 8.0), 20 mM of magnesium sulfate, 0.167 mM of the chromogenic substrate, and 20 μL of the lysate originating from *Tachypleus tridentatus* in 200 mL of a reaction solution. The plate was added with 25 μL of 100 ng/mL LAM or 25 μL of 1 ng/mL Et (originating from *E. coli* 0111, strain B4), followed by the reaction for 30 minutes in a Well Reader SK603. The rate of absorbance change per minute (mAbs/min) [A 405 nm-492 nm (control wavelength)] was automatically measured. The values obtained by the respective measurements were compared with a value obtained when the concentration of the Tris-HCl buffer was 50 mM (control value; assumed 100%), thereby the relative activities (%) of LAM and the relative activities (%) of Et were calculated. The results are shown in FIG. 9 and FIG. 10.

Figure 9:
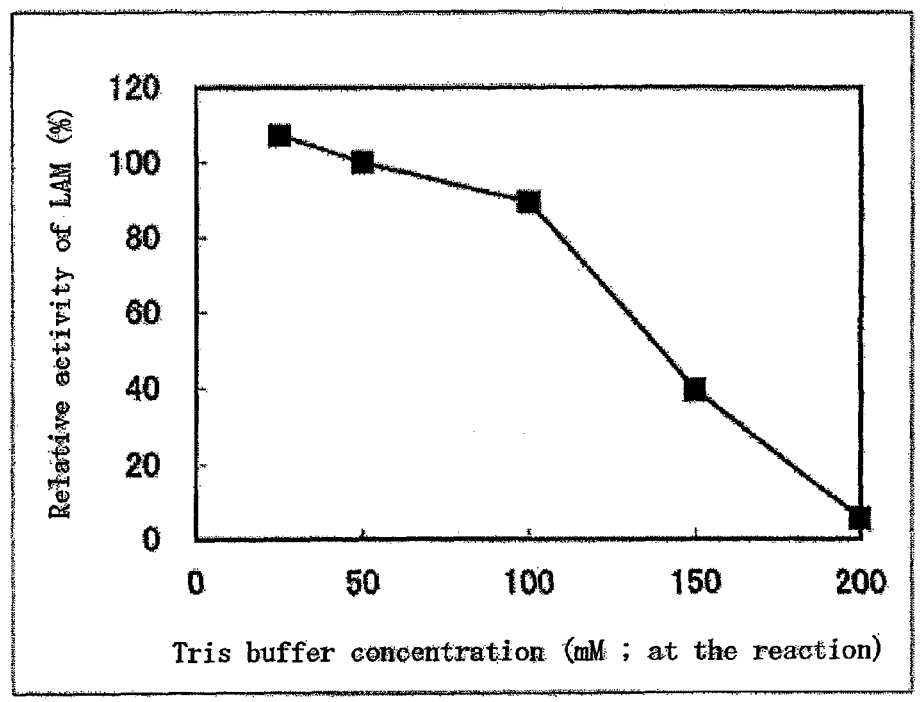
FIG. 9 is a diagram showing a relationship between the concentration of Tris-HCl buffer and the relative activity of LAM in a *Limulus* reaction with a lysate originating from *Tachypleus tridentatus*.
Figure 10:
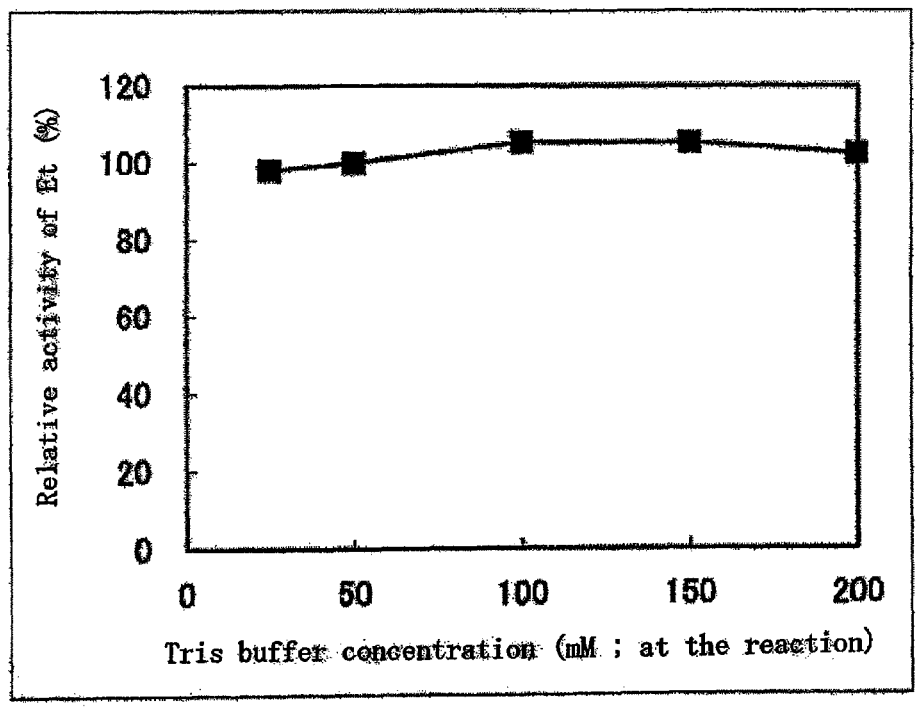
FIG. 10 is a diagram showing the relationship between the concentration of Tris-HCl buffer and the relative activity of Et in a *Limulus* reaction with a lysate originating from *Tachypleus tridentatus*.

When the concentration of the Tris-HCl buffer was 200 mM, the reactivity of LAM to the *Limulus* reagent was significantly inhibited as the relative activity of LAM showed 5.4% (i.e., the reactivity of LAM was eliminated by 94.6%) (FIG. 9). On the other hand, at this concentration, Et showed a relative activity of 102.5%. The reactivity of Et to the *Limulus* reagent was found to be dominantly retained compared with that of LAM (FIG. 10).

5-2. Example in which Lysate Originating from *Limulus polyphemus* is Used

An examination was carried out in a manner similar to that of the above section 5-1 except that a lysate originating from *Limulus polyphemus* was used instead of the lysate originating from *Tachypleus tridentatus* used in the above section 5-1. The results are shown in FIG. 11 and FIG. 12.

Figure 11:
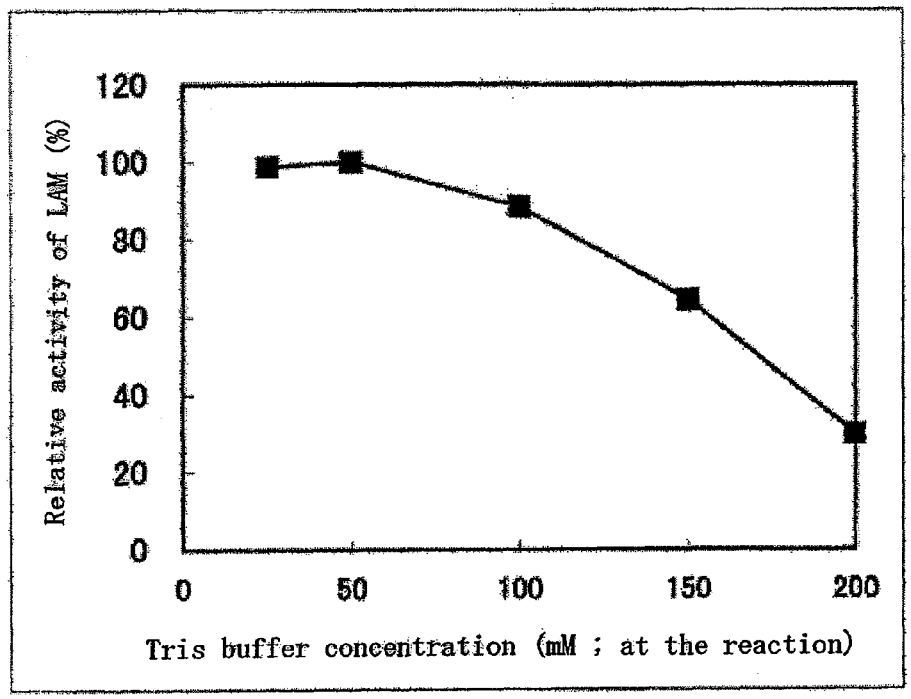
FIG. 11 is a diagram showing a relationship between the concentration of Tris-HCl buffer and the relative activity of LAM in a *Limulus* reaction with a lysate originating from *Limulus polyphemus*.
Figure 12:
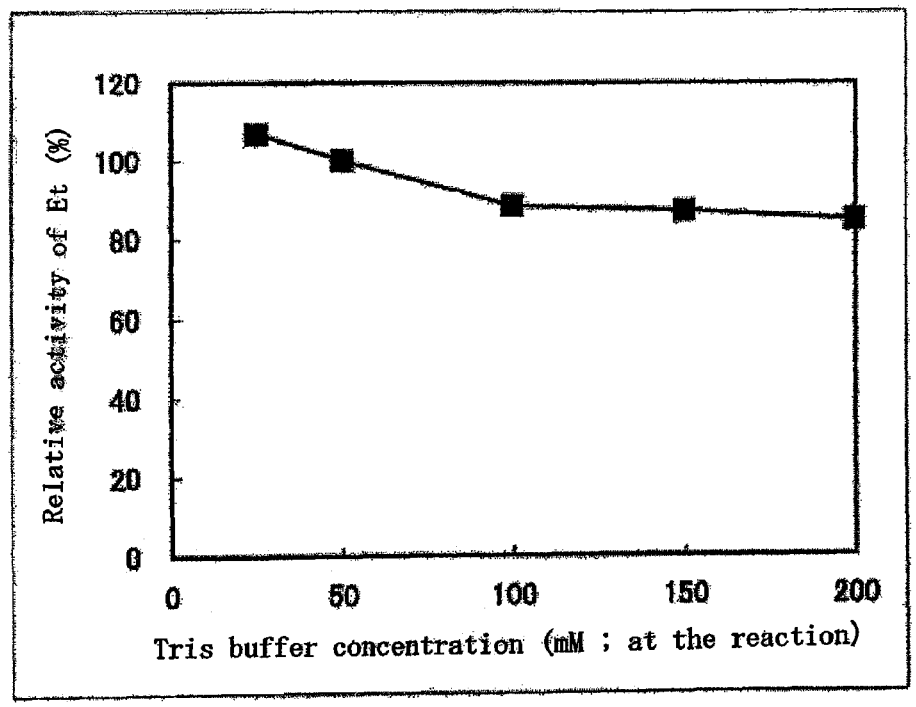
FIG. 12 is a diagram showing the relationship between the concentration of Tris-HCl buffer and the relative activity of Et in a *Limulus* reaction with a lysate originating from *Limulus polyphemus*.

When the concentration of the Tris-HCl buffer was 200 mM, the reactivity of LAM to the *Limulus* reagent was considerably inhibited as the relative activity of LAM showed 29.8% (FIG. 11). On the other hand, at this concentration, Et showed a relative activity of 85.0%. The reactivity of Et to the *Limulus* reagent was found to be dominantly retained as compared with that of LAM (FIG. 12).

6. Comparison Between Reactivities of LAM and Et to *Limulus* Reagent in the Presence of Any One of the Various Buffers Various buffers listed in Table 2 were used and the same experiments as those of the above sections 5-1 and 5-2 were carried out, thereby the relative activities of LAM and the relative activities of Et when the concentration of any one of the various buffers was 200 mM were calculated. The results are shown in Table 2.

TABLE 2

Relative activities of LAM and relative activities of Et in the presence of various buffers

| Lysate used | Buffer (pH 8.0) | Relative activity of LAM | Relative activity of Et |
|---|---|---|---|
| LAL-lysate | Tris | 10-41% (3Lot) | 98-85% (3Lot) |
| | HEPES | 6-21% (3Lot) | 28-18% (3Lot) |
| | TES | 20% (1Lot) | 88% (1Lot) |
| | HEPPSO | 20% (1Lot) | 83% (1Lot) |
| | Tricine | 50% (1Lot) | 109% (1Lot) |
| | Bicine | 53% (1Lot) | 110% (1Lot) |
| | Imidazole | 20% (1Lot) | 95% (1Lot) |
| TAL-lysate | Tris | 5-11% (3Lot) | 103-90% (3Lot) |
| | HEPES | 8-9% (3Lot) | 59-44% (3Lot) |
| | TES | 9% (1Lot) | 91% (1Lot) |
| | HEPPSO | 8% (1Lot) | 57% (1Lot) |
| | Tricine | 6% (1Lot) | 101% (1Lot) |
| | Bicine | 8% (1Lot) | 94% (1Lot) |
| | Imidazole | 5% (1Lot) | 72% (1Lot) |

(Note)
When assayed at a reaction solution amount of 200 μL.

As described above, a decrease in reactivity of LAM to a *Limulus* reagent in the presence of a metal salt or a buffer has become evident. Therefore, in the present invention, a quantitative assay of Et can be correctly carried out by assaying Et using a *Limulus* reagent while allowing Et to coexist with a metal salt or a buffer to eliminate the reactivity of LAM.

INDUSTRIAL APPLICABILITY

The elimination methods 1 and 2 of the present invention can be used for eliminating the influence of LAM on a *Limulus* reaction.

In addition, the Et-assay method, the disease detection method, the Et-assay kit, and the kit for diagnosing a disease of the present invention can be used in the assay and detection of Et and Et-associated diseases.

Elimination method 1 or 2 of the present invention allows the reactivity of LAM in an LAM-containing sample to a *Limulus* reagent to be eliminated simply, quickly, cheaply, and efficiently. In addition, the Et-assay method is able to assay Et in the sample without any influence of LAM or with a decreased influence of LAM. Further, the disease detection method allows the detection of Et-associated diseases with higher degree of accuracy. Further, the Et-assay kit and the kit for diagnosing a disease of the present invention allow the Et-assay method and the disease detection method described above to be carried out simply and quickly.

What is claimed is:

1. A method of assaying endotoxin in a sample containing lipoarabinomannan (LAM) and endotoxin using a Limulus reagent comprising:
   treating the sample with a metal salt in an amount sufficient to eliminate reactivity of LAM with a Limulus reagent;
   adding the Limulus reagent to the sample; and
   measuring the presence or absence of endotoxin by detecting the presence or absence of a Limulus reaction.

2. The method according to claim 1, wherein said metal salt is one or more metal salts selected from the group consisting of sulfate salts, metal chlorides, and nitrate salts.

3. The method according to claim 2, wherein said metal salt is one or more metal salts selected from the group consisting of sodium sulfate, magnesium sulfate, potassium sulfate, sodium chloride, magnesium chloride, potassium chloride, calcium chloride, sodium nitrate, and potassium nitrate.

4. The method according to claim 1, wherein said metal salt is coexistent at a final concentration of 30 to 500 mM in the sample.

5. The method according to claim 1, wherein said Limulus reagent is an endotoxin-specific Limulus reagent.

6. A method of assaying endotoxin in a sample containing lipoarabinomannan (LAM) and endotoxin using a Limulus reagent comprising:
   adding a buffer to the sample in an amount sufficient to eliminate reactivity of LAM with a Limulus reagent, whereby LAM reactivity is eliminated;
   adding the Limulus reagent to the sample; and
   measuring the presence or absence of endotoxin by detecting the presence or absence of a Limulus reaction.

7. The method according to claim 6, wherein said buffer is one or more buffers selected from the group consisting of tris(hydroxymethyl)aminomethane, 2-[4-(2-hydroxyethyl)-1-piperazinyl]ethanesulfonic acid, N-tris(hydroxymethyl)methyl-2-aminoethanesulfonic acid, 2-hydroxy-3-[4-(2-hydroxyethyl)-1-piperazinyl]propanesulfonic acid monohydrate, N-[tris(hydroxymethyl)methyl]glycine, N,N-bis(2-hydroxyethyl)glycine, and imidazole.

8. The method according to claim 6, wherein said buffer is coexistent at a final concentration of 100 to 300 mM in the sample.

9. A method of assaying endotoxin, comprising at least the following steps (a) and (b):

(a) adding a metal salt or a buffer to a sample containing endotoxin and lipoarabinomannan (LAM) in an amount sufficient to eliminate reactivity of LAM with a Limulus reagent; and (b) contacting the sample with a Limulus reagent after step (a) to detect a Limulus reaction initiated by endotoxin, wherein the concentration of the metal salt is 30 to 500 mM or the concentration of the buffer is 100 to 300 mM.

10. The method according to claim 9, wherein said Limulus reagent is an endotoxin-specific Limulus reagent.

11. A method of assaying endotoxin, comprising at least the following steps (a) and (b):

(a) mixing a Limulus reagent with a metal salt or a buffer wherein the amount of metal salt or buffer is sufficient to eliminate reactivity of lipoarabinomannan (LAM) with the Limulus regent; and (b) contacting a sample containing endotoxin and lipoarabinomannan with the mixture of step (a), thereby detecting a Limulus reaction initiated by endotoxin, wherein the concentration of the metal salt is 30 to 500 mM or the concentration of the buffer is 100 to 300 mM.

12. The method according to claim 11, wherein said Limulus reagent is an endotoxin-specific Limulus reagent.

* * * * *

UNITED STATES PATENT AND TRADEMARK OFFICE
CERTIFICATE OF CORRECTION

| | |
|---|---|
| PATENT NO. | : 7,638,340 B2 |
| APPLICATION NO. | : 11/993214 |
| DATED | : December 29, 2009 |
| INVENTOR(S) | : Tanaka et al. |

It is certified that error appears in the above-identified patent and that said Letters Patent is hereby corrected as shown below:

Column 18, Lines 50-51, "Limulus reagent, whereby LAM reactivity is eliminated;" should be changed to --Limulus reagent;--

Column 20, Line 1, "or a buffer" should be changed to --or a buffer,--

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,638,340 B2
APPLICATION NO. : 11/993214
DATED : December 29, 2009
INVENTOR(S) : Tanaka et al.

It is certified that error appears in the above-identified patent and that said Letters Patent is hereby corrected as shown below:

On the title page, item (73) Assignee:, "Seikagu Corporation," should be changed to --Seikagaku Corporation,--

Signed and Sealed this

Thirty-first Day of August, 2010

David J. Kappos
*Director of the United States Patent and Trademark Office*